(12) United States Patent
Patten et al.

(10) Patent No.: US 9,988,621 B2
(45) Date of Patent: Jun. 5, 2018

(54) METHOD OF ENZYME INACTIVATION

(75) Inventors: Anja Patten, Leichlingen (DE); Christof Nolde, Hilden (DE); Petra Vogt, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days. days.

(21) Appl. No.: 14/373,029

(22) PCT Filed: Feb. 15, 2012

(86) PCT No.: PCT/EP2012/052541
§ 371 (c)(1),
(2), (4) Date: Jul. 17, 2014

(87) PCT Pub. No.: WO2013/120515
PCT Pub. Date: Aug. 22, 2013

(65) Prior Publication Data
US 2015/0056679 A1 Feb. 26, 2015

(51) Int. Cl.
*C12N 9/99* (2006.01)
*C11D 3/386* (2006.01)
*C11D 3/39* (2006.01)
*C11D 11/00* (2006.01)
*B01D 65/02* (2006.01)

(52) U.S. Cl.
CPC ............. *C12N 9/99* (2013.01); *B01D 65/02* (2013.01); *C11D 3/386* (2013.01); *C11D 3/3945* (2013.01); *C11D 11/0017* (2013.01); *C11D 11/0023* (2013.01); *C12Y 301/01* (2013.01); *B01D 2321/166* (2013.01)

(58) Field of Classification Search
None
See application file for complete search history.

(56) References Cited

U.S. PATENT DOCUMENTS

| 6,197,739 B1 | 3/2001 | Oakes et al. |
| 7,001,873 B2 * | 2/2006 | McDonnell .......... A61K 31/327 422/13 |
| 8,344,026 B2 * | 1/2013 | Li et al. ........................ 514/557 |
| 8,809,392 B2 * | 8/2014 | Li et al. ........................ 514/557 |

FOREIGN PATENT DOCUMENTS

| WO | WO 96/23579 | 8/1996 |
| WO | WO 2009/118714 | * 10/2009 |

OTHER PUBLICATIONS

Calvez et al. (2010) J. Biol. Dyn. 4 (1), 28-42 (abstract only).*
Wallace AC et al. Derivation of 3D coordinate templates for searching structural databases: Application to Ser-His-Asp catalytic triads in the serine proteinases and lipases. 1996. Protein Science. 5:1001-1013.*

* cited by examiner

*Primary Examiner* — Paul J Holland
(74) *Attorney, Agent, or Firm* — Merchant & Gould P.C.

(57) ABSTRACT

The present invention relates to a method for the inactivation of enzymes with a composition comprising a sulfonated peroxycarboxylic acid according to formula (I) wherein: $R_1$ is hydrogen, or a substituted or unsubstituted $C_m$ alkyl group; $R_2$ is a substituted or unsubstituted $C_n$ alkyl group; X is a hydrogen atom, a cationic group, or an ester forming moiety; Y is a hydrogen atom, a cationic group, or an ester forming moiety; n is 1 to 10; m is 1 to 10; and n+m is less than or equal to 18, wherein the composition is contacted with the enzyme.

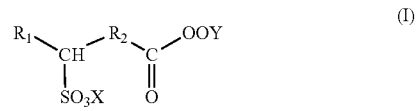

(I)

17 Claims, No Drawings

METHOD OF ENZYME INACTIVATION

FIELD OF THE INVENTION

The present invention relates to a chemical method of inactivating enzymes, in particular hydrolytic enzymes used in cleaning applications.

BACKGROUND

The use of enzymes, for example proteases and lipases, offers considerable advantages in cleaning applications. For example, WO 97/02753 A1 discloses that enzymes can be used to remove protein- and lipid-containing soils at low temperatures and without the need for additional chemicals. Thereby, the use of enzymes in cleaning applications increases the material compatibility, decreases the energy costs, reduces water consumption, and reduces the health and environmental risks that would result from the use of chemicals.

Enzyme-based cleaning products are used for example in the food industry, in particular for the cleaning-in-place of equipment used to process food or beverages. Here, cleaning-in-place refers to the cleaning of process equipment by circulating a cleaning solution through the equipment without the need to disassemble the equipment prior to the cleaning procedure. A particular example for the use of enzymes in cleaning applications is the use of proteolytic enzymes for the cleaning of membranes in used to process dairy products.

Enzymes can also be employed for the cleaning of textiles or other laundry articles at low temperatures.

A problem associated with the use of enzymes in the cleaning-in-place of food processing equipment is that they might contaminate and potentially degrade the foodstuff, if they are not completely inactivated after the cleaning step. For example, a lipase might degrade any dairy products coming into contact with the enzyme. This might change the taste of the foodstuff and potentially prevent its commercial use. Therefore, an effective and cost-efficient way to inactivate the enzymes is needed.

Similarly, residual enzymes in laundry-cleaning applications might degrade laundry components, especially if the laundry material is a textile of biological origin, e.g. wool, resulting in degradation products that have an unpleasant odour.

Proteases are commonly inactivated by very high or very low pH. Lipases, on the other hand, are less sensitive towards pH and require the combination of a pH lower than 2 and a temperature in the range of 40° C. to 70° C. for their inactivation. However, this method of inactivation is potentially damaging to the equipment that is to be cleaned. For example, an acid treatment might have a corrosive effect on the surfaces of process equipment and on filtration membranes used therein. Also, the rather high temperature required entails an increase in energy costs. Furthermore, the use of large volumes of acidic inactivation compositions requires their neutralization and proper disposal of the liquid waste.

Therefore, the technical object of the present invention is to provide a method of enzyme inactivation that affects a broad range of enzymes, that is effective at ambient temperature (i.e. 20° C. to 30° C.), that does not require strongly acidic or basic conditions, and that has a high material compatibility in order to be used in cleaning-in-place applications.

SUMMARY OF THE INVENTION

The present invention provides a method for the inactivation of enzymes with a composition comprising a sulfonated peroxycarboxylic acid according to formula 1.

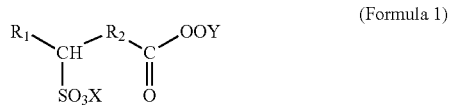

(Formula 1)

Wherein: $R_1$ is hydrogen, or a substituted or unsubstituted $C_m$ alkyl group; $R_2$ is a substituted or unsubstituted $C_n$ alkyl group; X is a hydrogen atom, a cationic group, or an ester forming moiety; Y is a hydrogen atom, a cationic group, or an ester forming moiety; n is 1 to 10; m is 1 to 10; and n+m is less than or equal to 18.

In a preferred embodiment, Y is a hydrogen atom.

In another embodiment, the composition further comprises an oxidizing reagent, which is not a chlorine-containing compound.

Preferably, the composition further comprises hydrogen peroxide as an oxidizing reagent.

The composition may further comprise a $C_1$ to $C_{22}$ carboxylic or peroxycarboxylic acid.

In a preferred embodiment, the enzymes are selected from the group of hydrolases.

Preferably, the enzymes are selected from the group consisting of proteases, lipases, glycosidases, or mixtures thereof.

The method may be used after at least one cleaning step using an enzyme-based cleaning product to inactivate the enzymes deriving from the cleaning product.

Preferably, the enzyme-based cleaning product is used for the cleaning-in-place of soiled process equipment, and the inactivation composition is contacted with the equipment.

The enzyme-based cleaning product may be used for the cleaning of microfiltration, ultrafiltration, nanofiltration and reverse osmosis membranes, and the inactivation composition may be contacted with those membranes.

In some embodiments, the membranes may consist of cellulose, cellulose acetate, nitrocellulose, polysulfone, polyethersulfone, fully aromatic polyamide, polyvinylidene fluoride, polytetrafluoroethylene, polyacrylnitrile, polypropylene, carbon, α-aluminium oxide, or zirconium oxide, combined with not further specified backing material.

The method may be carried out at a temperature that is in the range of 10° C. to 70° C.

DETAILED DESCRIPTION

The present invention relates to the use of sulfonated peroxycarboxylic acids and compositions thereof in the inactivation of enzymes. The sulfonated peroxycarboxylic acids, which have been described in US 2010/0021557 A1, can have a general structure according to formula 1:

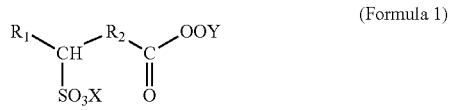

(Formula 1)

Wherein: $R_1$ is hydrogen, or a substituted or unsubstituted $C_m$ alkyl group; $R_2$ is a substituted or unsubstituted $C_n$ alkyl group; X is a hydrogen atom, a cationic group, or an ester forming moiety; Y is a hydrogen atom, a cationic group, or an ester forming moiety; n is 1 to 10; m is 1 to 10; and n+m is less than or equal to 18.

$R_1$ and $R_2$ may be unsubstituted or substituted alkyl groups. In preferred embodiments, $R_1$ and $R_2$ do not contain cyclic alkyl groups. Suitable substituents include for example hydroxyl groups, sulfonic acid groups, or epoxide groups.

Preferred embodiments of $R_1$ are for example a hydrogen atom, a methyl group, an unsubstituted $C_8$ or $C_9$ alkyl group, a $C_9$ or $C_{10}$ alkyl group substituted with at least one hydroxyl group, or a $C_9$ or $C_{10}$ alkyl group including at least one epoxide group. Preferred embodiments for $R_2$ are for example a $C_6$ to $C_9$ unsubstituted alkyl group, a $C_8$ or $C_9$ alkyl group substituted with at least one hydroxyl group, a $C_8$ or $C_9$ alkyl group substituted with at least one sulfonic acid group, or a $C_9$ group including at least one epoxide group.

In some embodiments, the composition of the present invention can include a mixture of two or more of the sulfonated peroxycarboxylic acids.

The following table shows examples of preferred embodiments of sulfonated peroxycarboxylic acids suitable for use in the composition of the present invention. In some embodiments, the composition of the present invention includes a sulfonated peroxycarboxylic acid that is selected from the group consisting of the compounds shown in this table, or salts and mixtures thereof.

| ID | Structure and name of compound |
|---|---|
| A | 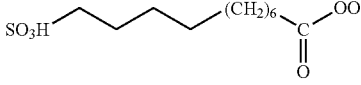<br>11-Sulfo-undecaneperoxoic acid |
| B | 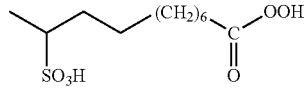<br>10-Sulfo-undecaneperoxoic acid |
| C | 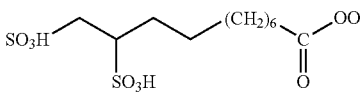<br>10,11-Disulfo-undecaneperoxic acid |
| D | 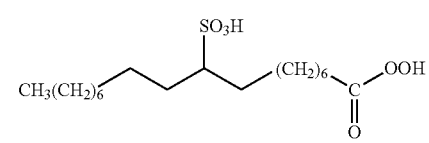<br>9-Sulfo-octadecaneperoxoic acid |
| E | 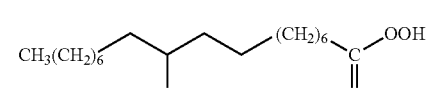<br>10-Sulfo-octadecaneperoxoic acid |
| F | 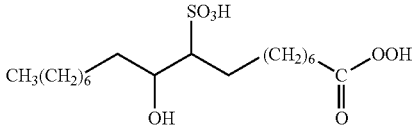<br>10-Hydroxy-9-sulfo-octadecaneperoxoic acid |
| G | 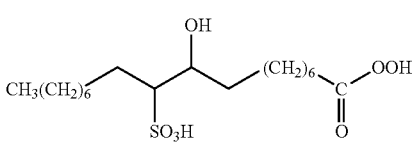<br>9-Hydroxy-10-sulfo-octadecaneperoxoic acid |
| H | 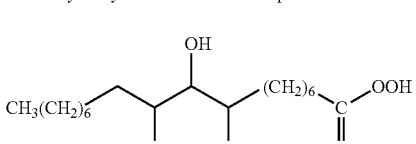<br>9,10-Dihydroxy-8-sulfo-octadecaneperoxoic acid |
| I | 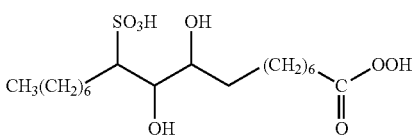<br>9,10-Dihydroxy-11-sulfo-octadecaneperoxoic acid |
| J | 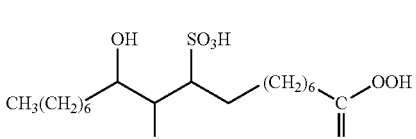<br>10,11-Dihydroxy-9-sulfo-octadecaneperoxoic acid |
| K | 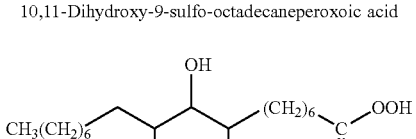<br>8,9-Dihydroxy-10-sulfo-octadecaneperoxoic acid |
| L | 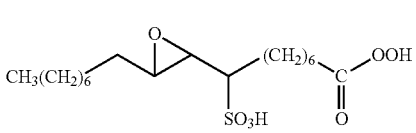<br>8-(3-octyloxiran-2-yl)-8-sulfo-octaneperoxoic acid |
| M | 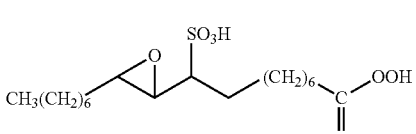<br>9-(3-heptyloxiran-2-yl)-9-sulfo-nonaneperoxoic acid |

| ID | Structure and name of compound |
|---|---|
| N | CH₃(CH₂)₆-[epoxide with SO₃H]-（CH₂)₆-C(=O)OOH<br>8-(3-(1-sulfo-octyl)-oxiran-2-yl)-octaneperoxoic acid |
| O | CH₃(CH₂)₆-CH(SO₃H)-CH(SO₃H)-(CH₂)₆-C(=O)OOH<br>9,10-Disulfo-octadecaneperoxoic acid |

The sulfonated peroxycarboxylic acids may be prepared from, for example, sulfonated fatty acids or from non-sulfonated fatty acids, which can be sulfonated. If non-sulfonated fatty acids are used as a starting material, they may be sulfonated prior to their conversion to the peroxycarboxylic acid form or they may be sulfonated at the same time or after formation of the peroxycarboxylic acid form. Sulfonation may be carried out by any method known to a person skilled in the art.

Preferred sulfonated fatty acids for use in forming compounds of the present invention are for example, 11-sulfo-undecanoic acid, 10,11-disulfo-undecanoic acid, sulfonated oleic acid, sulfonated linoleic acid, sulfonated palmitoleic acid, or sulfonated stearic acid.

The peroxycarboxylic acid can be formed using a variety of reaction mechanisms. For example, in some embodiments, the percarboxylic acid is formed by the direct acid catalyzed equilibrium action of hydrogen peroxide with the starting material.

In a preferred embodiment sulfonated oleic acid is used as a starting material. It is thought that because sulfonated oleic acid is derived from natural sources, it is not chemically pure, i.e. it does not contain only one form of sulfonated oleic acid. Therefore, the peroxycarboxylic form of the sulfonated oleic acid may comprise a mixture of compounds F, G, J, K from the above table.

The sulfonated peroxycarboxylic acids of the present invention may be present in a composition comprising one or more additional components. In a preferred embodiment the composition additionally includes oxidizing reagents, carboxylic and percarboxylic acids, surfactants, and stabilizing agents. The composition of the present invention may also be used in conjunction with conventional cleaning agents, for example alkaline detergents, or compositions containing urea, nitric acid, phosphoric acid, or mixtures thereof.

The composition of the present invention may comprise at least one oxidizing agent. The oxidizing agent may be an organic or an inorganic oxidizing agent. Examples for suitable inorganic oxidizing agents are hydrogen peroxide, inorganic peroxides such as for example sodium peroxide, perborates such as for example sodium perborate, salts of monoperoxopersulfuric acid such as for example potassium monopersulfate, adducts of hydrogen peroxide to inorganic compounds such as for example sodium percarbonate, as well as adducts of hydrogen peroxide to sodium phosphates. Examples for suitable organic oxidizing agents include peroxycarboxylic acids such as for example peroxyacetic acid. In a preferred embodiment, the composition of the present invention comprises hydrogen peroxide as an oxidizing reagent.

The composition of the present invention may comprise at least one carboxylic acid in addition to the sulfonated peroxycarboxylic acid. The carboxylic acid may be any $C_1$ to $C_{22}$ carboxylic acid. The carboxylic acid may be saturated or unsaturated. Examples for suitable monocarboxylic acids are formic, acetic, propionic, butyric, pentanoic, hexanoic, heptanoic, octanoic, nonanoic, decanoic, undecanoic, dodecanoic, tetradecanoic, hexadecanoic, octadecanoic, or icosanoic acid, as well as their branched isomers such as for example neopentanoic, neoheptanoic, or neodecanoic acid. Examples for suitable dicarboxylic acids are oxalic, malonic, succinic, glutaric, adipic, pimelic, or suberic acid. Examples for suitable tricarboxylic acids are citric acid or isocitric acid. Examples for suitable hydroxy carboxylic acids are hydroxyacetic or lactic acid. Other examples for suitable carboxylic acids are ascorbic acid or maleic acid.

The composition of the present invention may also include the peroxycarboxylic forms of any of the carboxylic acids mentioned above. The peroxycarboxylic form may be prepared by any method known in the art, for example by combining the carboxylic acid with hydrogen peroxide. A solution of peroxyoctanoic acid can for example be obtained by combining octanoic acid and hydrogen peroxide and a hydrotrope, solvent or carrier.

The composition of the present invention may include one ore more surfactants. In general, all kinds of surfactants known in the art are appropriate in the present invention, like for example anionic surfactants, non-ionic surfactants, cationic surfactants, and amphiprotic surfactants. A suitable surfactant is for example sodium cumene sulfonate.

The composition of the present invention may include one ore more stabilizing agents. The stabilizing agents serve to stabilize the peroxycarboxylic acid and peroxide compounds of the present composition. Suitable stabilizing agents include, for example, metal cation chelating agents. Examples for chelating agents include aminopolycarboxylic acids, such as ethylenediamine tetraacetic acid, or polyphosphonic acids and aminopolyphosphonic acids, such as hydroxyethane diphosphonic acid, ethylenediamine tetramethylene phosphonic acid and diethylene triamine pentamethylene phosphonic acid, and water-soluble salts thereof.

In a preferred embodiment, the composition of the present invention includes 10% to 20% by weight of sulfonated oleic acid, up to 10% by weight of acetic acid, 5% to 10% of peracetic acid, 1% to 5% by weight of octanoic acid, 1% to 5% by weight of peroxyoctanoic acid, 1% to 5% by weight of hydroxyethane diphosphonic acid, and 8% to 35% by weight of hydrogen peroxide.

According to the present invention, the composition described above can be used to inactivate enzymes. Preferably, the enzymes that may be inactivated using the present invention are hydrolases such as, for example, proteases, lipases, nucleases, or glycosidases. The enzymes may be part of an enzyme composition, comprising any of the enzymes described herein or mixtures thereof. Preferably, the enzyme composition is used in alkaline conditions, more preferably of pH 7 to pH 9.

Proteases may include, for example, those of animal, vegetable, or microbial origin. Chemically or genetically modified proteases are also included. Preferably, proteases include serine proteases, for example subtilisins or trypsin-like proteases. More preferably, the proteases are subtilisins derived from, for example, alkalophilic *Bacillus*. sp., *Aspergillus* sp., *Bacillus licheniformis*, or *Bacillus lentus*, or variants of those subtilisins.

Lipases may include, for example, those of fungal or bacterial origin. Chemically or genetically modified lipase mutants are also included. Preferably, lipases are derived from, for example, *Humicola lanuginosa, Pseudomonas mendocina, Chromobacter*, or *Rhizopus arrhizus*. More preferably, lipases include those derived from *Humincola lanuginosa*, or variants thereof. Lipases may also include phospholipases, such as, for example, those obtained from bovine or porcine pancreas, from snake or bee venom, or those deriving from microbial origin, and other types of lipolitic enzymes such as, for example, cutinases.

Glycosidases may include amylases and cellulases. Amylases include, for example, those of fungal or bacterial origin. Chemically or genetically modified amylase mutants are also included. Preferably, amylases are derived from, for example, *Bacillus amyloliquefaciens* or thermostable *Bacillus licheniformis*. Cellulases include, for example, those of fungal or bacterial origin. Chemically or genetically modified cellulase mutants are also included. Preferably, cellulases are derived from, for example, *Humicola insolens* or *Trichoderma longibrachiatum*. Preferably, cellulases include those that have a pH optimum between pH 5 and pH 9.5.

The present invention may be used to inactivate enzymes, which are, for example, in solution or immobilized on any kind of substrate. The inactivation may be achieved, for example, by mixing the composition of the present invention with the enzyme solution, or by contacting the composition with the substrate.

In a preferred embodiment, the present invention discloses a method to inactivate enzymes derived from an enzyme-based cleaning product. This may, for example, be achieved by contacting the cleaning product with the composition of the present invention. The composition of the present invention may also be contacted with an object that has been contacted with the cleaning product in a preceding step to inactivate any residual enzyme that is left on the object. It is possible to apply the composition directly after use of the cleaning product, or to perform any number of additional cleaning steps (e.g. flushing) between application of the cleaning product and of the composition.

Preferably, the composition of the present invention is used to inactivate enzymes on process equipment.

Process equipment includes equipment that is used for the processing of food and beverages, such as, for example, that used for dairy, food and beverage processing, in slaughter houses, in breweries, for fish or fish meal production, or for animal feed production or feed pelleting. Preferably, the composition is used as part of a cleaning-in-place procedure, wherein the cleaning product and the composition are circulated through the equipment, without prior disassembly of the equipment.

The composition of the present invention may also be used to inactivate enzymes in processes such as enzymatic cleaning of fabrics and textiles or in surface cleaning of kitchen or hospital environments.

As a particular example, the composition of the present invention may be used to inactivate enzymes used for the cleaning of laundry articles. Laundry articles may be soiled fabrics or textiles that are cleaned by agitating the articles in a cleaning product, e.g. an enzyme-containing detergent solution, for a certain period of time followed by rinsing the articles with water. The composition for the inactivation of the enzymes deriving from the cleaning product may be contacted with the laundry before the rinsing step, or it may be applied after the rinsing step and then be followed by an additional rinsing step. The cleaning procedure may be performed in an automatized washing machine or it may be performed as a hand wash. In particular, the cleaning procedure may be part of an on-premise laundry application.

The composition may also be used to inactivate enzymes on membranes that are used, for example, in any of the food processing applications described above. Membranes include, for example, ultrafiltration, microfiltration, nanofiltration and reverse osmosis membranes. The membranes may be part of a process equipment, which is cleaned in a cleaning-in-place procedure. The membranes may consist of, for example, cellulose, cellulose acetate, nitrocellulose, polysulfone, polyethersulfone, fully aromatic polyamide, polyvinylidene fluoride, polytetrafluoroethylene, polyacrylnitrile, polypropylene, carbon, anorganic membrane materials, such as α-aluminium oxide or zirconium oxide, and may include not further specified backing material.

Enzyme inactivation according to the present invention may be carried out at a temperature from 5° C. to 95° C., preferably from 10° C. to 60° C., more preferably from 20° C. to 30° C.

EXAMPLES

Inactivation of Lipases on Microfiltration Membranes

Tests of lipase inactivation were conducted on a DDS M38 flat sheet MF/UF lab test plant. Microfiltration membranes of type Alfa Laval GRM 0.2 were incubated for 30 minutes to 60 minutes at 50° C. by circulating an aqueous solution containing 0.2% of an enzyme composition at pH 9. The enzyme composition contained 5% to 10% by weight of Rizolipase (a lipase from *Rhizopus arrhizus*) and 5% to 10% by weight of Subtilisin. Subsequently, the membranes were subjected to one of the cleaning and inactivation procedures described below. Immediately before and after the cleaning and inactivation procedures, samples of the membranes were frozen and stored frozen until the analysis of lipase concentration and activity. Analysis of lipase concentration and activity was performed by enzyme-linked immunosorbent assays (ELISA) by Novozymes A/S. Lipase concentration is reported as μg of lipase per g of membrane, the specific lipase activity is reported as KLU per g of lipase.

In procedure 1 (comparative example), membranes were treated by circulating an aqueous solution containing 0.1% by weight of urea, 24% by weight of phosphoric acid, and 29% by weight of nitric acid, supplemented with 0.3% by weight of an aqueous solution containing 26.7% by weight of hydrogen peroxide, 6.7% by weight of acetic acid, and 4.5% by weight of peracetic acid. Circulation was carried out for 30 minutes at 25° C. This treatment reduced the lipase concentration from 295 μg/g to 44 μg/g and its specific activity from 1.7 KLU/g to 0.26 KLU/g.

In procedure 2 (comparative example), membranes were treated by circulating an aqueous solution containing 0.1% by weight of urea, 24% by weight of phosphoric acid, and 29% by weight of nitric acid, supplemented with 0.3% by weight of an aqueous solution containing 5.1% by weight hydrogen peroxide, 42.09% by weight of acetic acid, 8.6% by weight of peracetic acid, 3.37% by weight of octanoic acid, and 0.7% by weight of peroctanoic acid. Circulation was carried out for 30 minutes at 25° C. This treatment reduced the lipase concentration from 229 μg/g to 1.91 μg/g and its specific activity from 1.4 KLU/g to 0.011 KLU/g.

In procedure 3, membranes were treated by circulating an aqueous solution containing 0.1% by weight of urea, 24% by weight of phosphoric acid, and 29% by weight of nitric acid, supplemented with 0.3% by weight of an aqueous solution according to the present invention containing 8-35% by weight of Hydrogen peroxide, 10-20% by weight of sulfonated oleic acid, less than 10% by weight of acetic acid, 5-10% by weight of peracetic acid, 1-5% by weight of octanoic acid, 1-5% by weight of hydroxyethane diphosphonic acid, and 1-5% by weight of peroxyoctanoic acid. Circulation was carried out for 30 minutes at 25° C. This treatment reduced the lipase concentration from 220 µg/g to a level below the detection limit and its specific activity from 1.3 KLU/g to a level below the detection limit.

In procedure 4 (comparative example), membranes were treated by circulating an aqueous solution containing 0.1% by weight of urea, 24% by weight of phosphoric acid, and 29% by weight of nitric acid. Circulation was carried out for 30 minutes at 50° C. This treatment reduced the lipase concentration from 314 µg/g to 0.1 µg/g and its specific activity from 1.8 KLU/g to 0.0006 KLU/g.

The following table summarizes the results of the lipase concentration and activity measurements for each procedure. Please note that procedures 1, 2 and 4 are comparative examples, and that procedure 3 represents a method according to the present invention.

| Procedure | Lipase concentration (µg protein/g membrane) | | Lipase activity (KLU/g protein) | |
|---|---|---|---|---|
| | Before treatment | After treatment | Before treatment | After treatment |
| 1 | 295 | 44 | 1.7 | 0.26 |
| 2 | 229 | 1.91 | 1.4 | 0.011 |
| 3 | 220 | n.d. | 1.3 | n.d. |
| 4 | 314 | 0.1 | 1.8 | 0.0006 |

This test demonstrates that the procedure using a composition comprising a sulfonated peroxycarboxylic acid according to the present invention effectively inactivates lipases derived from an enzyme-based cleaning product at a temperature of 25° C. Furthermore, this procedure is more effective than any of the other procedures tested, shown by the fact that lipase concentration and activity were reduced to below the detection limit of the ELISA test in procedure 3. In particular, the composition of the present invention inactivates enzymes more effectively than compositions comprising peroxycarboxylic acids only (procedures 1 and 2) or a conventional acidic treatment at 50° C. (procedure 4).

The invention claimed is:

1. A method for the inactivation of enzymes, said method comprising:
    applying an enzyme-based cleaning composition comprising a lipase to a surface; and
    applying an enzyme-inactivation composition to said surface, wherein said enzyme-inactivation composition comprises a sulfonated peroxycarboxylic acid according to formula 1:

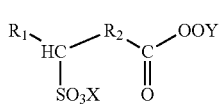

(formula 1)

wherein: R1 is hydrogen, or a substituted or unsubstituted Cm alkyl group; R2 is a substituted or unsubstituted Cn alkyl group; X is a hydrogen atom, a cationic group, or an ester forming moiety; Y is a hydrogen atom, a cationic group, or an ester forming moiety; n is 1 to 10; m is 1 to 10; and n+m is less than or equal to 18,
wherein said enzyme-inactivation composition is effective for inactivation of said lipase as determined by an ELISA analysis.

2. The method of claim 1, wherein Y is a hydrogen atom.

3. The method of claim 1, wherein said enzyme-inactivation composition further comprises an oxidizing reagent, wherein said oxidizing reagent is not a chlorine-containing compound.

4. The method of claim 1, wherein said enzyme-inactivation composition further comprises hydrogen peroxide.

5. The method of claim 1, wherein said enzyme-inactivation composition further comprises a C1 to C22 carboxylic or peroxycarboxylic acid.

6. The method of claim 1, wherein said applying an enzyme-inactivation composition to said surface is carried out at a temperature in the range of 10° C. to 70° C.

7. The method of claim 1, wherein said enzyme-inactivation composition has a pH of 7 to 9.

8. The method of claim 1, wherein said enzyme-inactivation composition further comprises:
    10 to 20 wt-% sulfonated oleic acid;
    up to 10 wt-% acetic acid;
    5 to 10 wt-% peracetic acid;
    1 to 5 wt-% octanoic acid;
    1 to 5 wt-% peroxyoctanoic acid;
    1 to 5 wt-% hydroxyethane diphosphonic acid; and
    8 to 35 wt-% hydrogen peroxide.

9. The method of claim 1, wherein said enzyme-inactivation composition of formula 1 is selected from 11-sulfo-undecanoic acid, 10,11-disulfo-undecanoic acid, sulfonated oleic acid, sulfonated linoleic acid, sulfonate palmitoleic acid, and sulfonated stearic acid.

10. The method of claim 1, wherein said surface comprises a surface on process equipment.

11. The method of claim 10, wherein said surface comprises a food or beverage preparation surface.

12. The method of claim 1, wherein said surface comprises a fabric or textile.

13. The method of claim 1, wherein said surface comprises a membrane.

14. The method of claim 1, wherein applying said enzyme-based cleaning composition comprises a clean-in-place procedure.

15. The method of claim 1, further comprising rinsing said surface after applying the enzyme-based cleaning composition to said surface.

16. The method of claim 1, wherein said enzyme-inactivation composition is effective for inactivating enzymes at room temperature.

17. The method of claim 1, wherein said enzyme-inactivation composition is applied to said surface at room temperature.

* * * * *

UNITED STATES PATENT AND TRADEMARK OFFICE
CERTIFICATE OF CORRECTION

PATENT NO. : 9,988,621 B2  
APPLICATION NO. : 14/373029  
DATED : June 5, 2018  
INVENTOR(S) : Patten et al.

Page 1 of 1

It is certified that error appears in the above-identified patent and that said Letters Patent is hereby corrected as shown below:

On the Title Page

Notice, Line 3: "by 0 days. days." should read --by 0 days.--

In the Claims

Column 10, Line 39, Claim 9: "acid, sulfonate palmitoleic" should read --acid, sulfonated palmitoleic--

Signed and Sealed this  
Twenty-eighth Day of April, 2020

Andrei Iancu  
*Director of the United States Patent and Trademark Office*